United States Patent
Catozzi et al.

(10) Patent No.: US 8,637,708 B2
(45) Date of Patent: Jan. 28, 2014

(54) PROCESS FOR PREPARING CINACALCET

(75) Inventors: Nicola Catozzi, Vicenza (IT); Livius Cotarca, Udine (IT); Johnny Foletto, Verona (IT); Massimiliano Forcato, Padua (IT); Roberto Giovanetti, Vicenza (IT); Giorgio Soriato, Verona (IT); Massimo Verzini, Verona (IT)

(73) Assignee: Zach System S.p.A., Bresso (Milan) (IT)

(*) Notice: Subject to any disclaimer, the term of this patent is extended or adjusted under 35 U.S.C. 154(b) by 0 days.

(21) Appl. No.: 13/395,326

(22) PCT Filed: Sep. 8, 2010

(86) PCT No.: PCT/EP2010/063154
§ 371 (c)(1), (2), (4) Date: May 24, 2012

(87) PCT Pub. No.: WO2011/029833
PCT Pub. Date: Mar. 17, 2011

(65) Prior Publication Data
US 2012/0238778 A1 Sep. 20, 2012

(30) Foreign Application Priority Data
Sep. 10, 2009 (EP) .................... 09169934

(51) Int. Cl.
*C07C 211/00* (2006.01)

(52) U.S. Cl.
USPC ..................................... 564/366

(58) Field of Classification Search
None
See application file for complete search history.

(56) References Cited

U.S. PATENT DOCUMENTS

| | | |
|---|---|---|
| 5,504,253 A | 4/1996 | Van Wagenen et al. |
| 6,011,068 A | 1/2000 | Nemeth et al. |
| 6,211,244 B1 | 4/2001 | Van Wagenen et al. |
| 7,250,533 B2 | 7/2007 | Lifshitz-Liron et al. |
| 7,294,735 B2 | 11/2007 | Lifshitz-Liron et al. |
| 7,393,967 B2 | 7/2008 | Lifshitz-Liron et al. |
| 2007/0259964 A1 | 11/2007 | Lifshitz-Liron et al. |

FOREIGN PATENT DOCUMENTS

| | | |
|---|---|---|
| EP | 1 990333 A1 | 11/2008 |
| EP | 2022777 A2 | 2/2009 |
| WO | 2007127449 A1 | 11/2007 |
| WO | 2008035212 A2 | 3/2008 |
| WO | 2009002427 A2 | 12/2008 |
| WO | 2009025792 A2 | 2/2009 |
| WO | 2009039241 A2 | 3/2009 |
| WO | 2010049293 A2 | 5/2010 |
| WO | 2010094674 A2 | 8/2010 |

OTHER PUBLICATIONS

Sorbera, R.M., "Cinacalcet Hydrochloride", Drugs of the Future, 2002, pp. 831-836.
Wang, X., et al., Synthesis of Cinacalcet congeners, Science Direct, Aug. 2004, pp. 8355-8358.
Bijukumar, G., et al., "Efficient Synthesis of Cinacalcet Hydrochloride", Synthetic Communications, Nov. 2007, pp. 1512-1517.
Thiel, O., et al., "Practical synthesis of the calcimimetic agent, cinacalcet", Science Direct, Oct. 2007, pp. 13-15.

*Primary Examiner* — Clinton Brooks
(74) *Attorney, Agent, or Firm* — Lucas & Mercanti, LLP

(57) ABSTRACT

A process for preparing N-[(1R)-1-(1-naphthyl)ethyl]-3-[3-(trifluoromethyl)-phenyl]propan-1-amine of formula hydrochloride salt of formula (I)

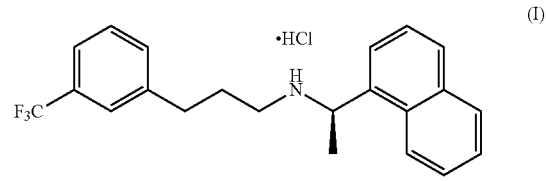

i.e. Cinacalcet.HCl and its intermediate of formula (IX)

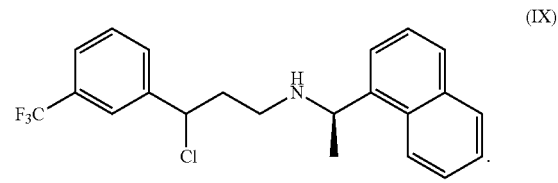

18 Claims, No Drawings

PROCESS FOR PREPARING CINACALCET

This application is a U.S. national stage of PCT/EP2010/063154 filed on Sep. 8, 2010 which claims priority to and the benefit of EP Application No, EP09169934,8 filed on Sep. 10, 2009.

The invention relates to a process for preparing the active product ingredient Cinacalcet, its intermediates and its pharmaceutically acceptable hydrochloride salt. Cinacalcet (CNC), namely N-[(1R)-1-(1-naphthyl)ethyl]-3-[3-(trifluoromethyl)-phenyl]propan-1-amine is used in therapy as hydrochloride salt of formula (I)

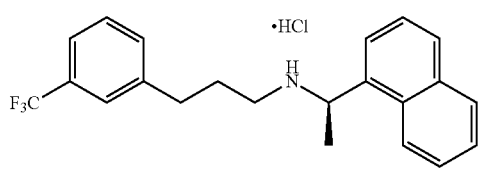

(I)

The hydrochloride salt of Cinacalcet (CNC.HCl), marketed as MIMPARA™ in the European Union, is a calcimimetic agent that decreases the secretion of parathyroid hormone by activating calcium receptors.

MIMPARA™ is approved for the treatment of secondary hyperparathyroidism (SHPT) in patients with chronic kidney disease receiving dialysis and for the treatment of primary hyperparathyroidism (PHPT) in patients for whom parathyroidectomy is not clinically appropriate or contraindicated.

U.S. Pat. No. 6,011,068 discloses a class of arylalkylamines comprising generically Cinacalcet and salts thereof.

U.S. Pat. No. 6,211,244 describes specifically Cinacalcet or a pharmaceutically acceptable salt or complex thereof as the compound 22J. U.S. Pat. No. 6,211,244 also discloses synthetic methods for preparing calcium receptor-active molecules, such a those having analogue structure of Cinacalcet, by a reductive amination approach comprising the condensation of the appropriate aromatic aldehyde or ketone with the suitable aryl amine followed by reduction with sodium cyanoborohydride (NaBH$_3$CN) or sodium triacetoxyborohydride, or by a diisobutyl aluminium hydride (DIBAL-H) mediated condensation of an aromatic amine with an aryl nitrile, followed by the reduction of the intermediate aluminium-imine complex with sodium cyanoborohydride or sodium borohydride. The method for condensing a nitrile with a primary or a secondary amine in the presence of diisobutyl aluminium hydride to form the corresponding imine was generically disclosed in the U.S. Pat. No. 5,504,253.

The preparation of Cinacalcet, described in Scheme 1 of *Drugs of the Future* 2002, 27(9), 831-836, (2002), comprises the reaction of 1(R)-(1-naphthyl)ethylamine (R-NEA) with 3-[3-(trifluoromethyl)phenyl]propionaldehyde by means of titanium tetraisopropoxide (Ti(O-i-Pr)$_4$) to give the corresponding imine, which is finally reduced with sodium cyanoborohydride in ethanol, as depicted in the following Scheme 1:

Scheme 1

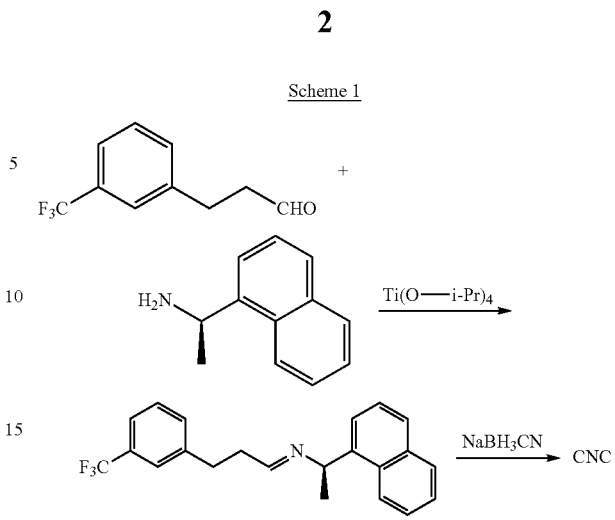

*Tetrahedron letters*, (45), 8355-8358, (2004) footnote 12, discloses the preparation of the starting material 3-[3-(trifluoromethyl)phenyl]propionaldehyde by reduction of 3-(trifluoromethyl) cinnamic acid to the corresponding alcohol followed by oxidation to give the desired aldehyde, as depicted in the following Scheme 2:

Scheme 2

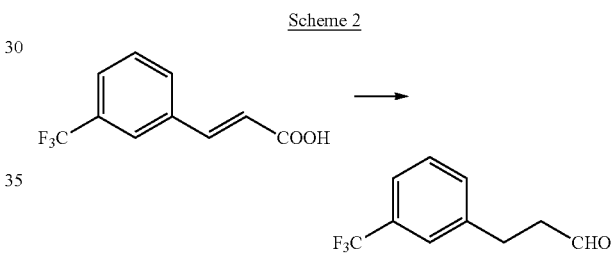

According to *Synthetic Communications*, 38: 1512-1517 (2008), the above synthesis of Cinacalcet involves the use of reagents such as Ti(O-i-Pr)$_4$ and DIBAL-H, which have to be handled in large volumes because the Cinacalcet has to be prepared on commercial scale and the handling of this moisture-sensitive and pyrophoric reagents on a large scale makes the synthesis more strenuous.

International patent application WO 2008/035212 discloses an alternative process for preparing 3-[3-(trifluoromethyl)phenyl]propionaldehyde, which comprises the oxidation of 3-[3-(trifluoromethyl)phenyl]propan-1-ol.

U.S. Pat. No. 7,250,533 discloses another process for preparing Cinacalcet, which comprises converting the hydroxyl moiety of 3-[3-(trifluoromethyl)phenyl]propanol into a good leaving group and combining the resulting compound with (R)-(1-naphthyl)ethylamine preferably in the presence of a base, according to the following Scheme 3:

Scheme 3

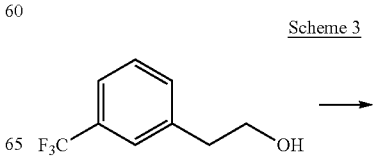

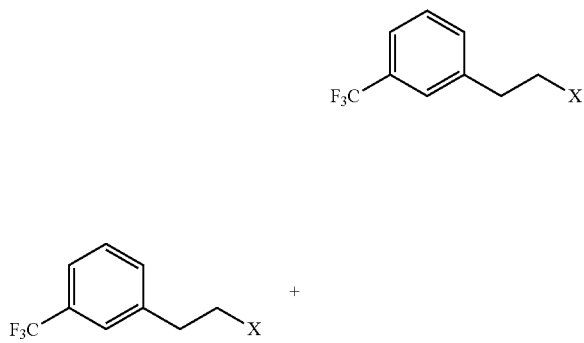

X = good leaving group

According to U.S. Pat. No. 7,294,735, Cinacalcet carbamate may be formed in various amounts while using different solvents during the synthesis of Cinacalcet as described in the above U.S. Pat. No. 7,250,533. U.S. Pat. No. 7,294,735 discloses a process for the preparation of Cinacalcet hydrochloride, containing Cinacalcet carbamate in an amount of about 0.03 area percent to about 0.15 area percent as measured by a chromatographic method, comprising the steps of (a) dissolving Cinacalcet, containing Cinacalcet carbamate in an amount of about 3 area percent to about 6 area percent as determined by a chromatographic method, in acetone, a linear or a branch-chain $C_{2-8}$ ether, mixtures thereof or with water; (b) adding hydrogen chloride to obtain a precipitate; and (c) recovering the Cinacalcet hydrochloride.

US patent application No. 2007/259964 provides a process for preparing Cinacalcet comprising reducing 3-(trifluoromethyl)cinnamic acid to obtain 3-(3-trifluoromethylphenyl)-propanoic acid, optionally converting 3-(3-trifluoromethylphenyl)-propanoic acid into a suitable acid derivative and combining the 3-(3-trifluoromethylphenyl)-propanoic acid or, if the case, said derivative with (R)-(1-naphthyl)ethylamine to give (R)—N-(1-(naphthalen-1-yl)ethyl)-3-(3-(trifluoromethyl)phenyl)propanamide and reducing (R)—N-(1-(naphthalen-1-yl)ethyl)-3-(3-(trifluoromethyl)phenyl) propanamide to Cinacalcet, according to the following Scheme 4:

*Tetrahedron letters*, (49), 13-15, (2008), discloses a synthetic sequence to Cinacalcet hydrochloride comprising reduction of 3-(trifluoromethyl)cinnamic acid in the presence of palladium hydroxide to obtain 3-(3-trifluoromethylphenyl)-propanoic acid, which is coupled with (R)-1-(1-naphthyl)ethylamine to the corresponding amide. The amide is then reduced in the presence of boron trifluoride-THF and sodium borohydride as reducing agents. After complete conversion, the resulting amine-borane complex is hydrolyzed by the addition of water and the crude Cinacalcet extracted into toluene is reacted with hydrochloric acid to give Cinacalcet hydrochloride, according to the following Scheme 5:

-continued

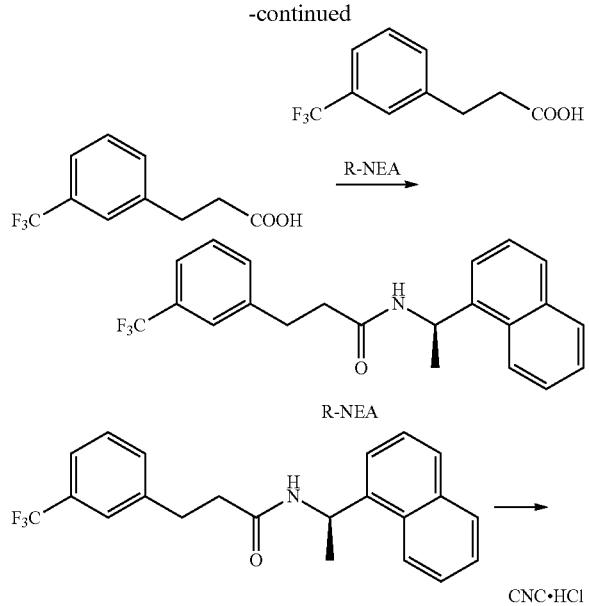

In patent application No. 2007MU00555 and *Synthetic Communications*, 38: 1512-1517 (2008) is disclosed another process for preparing Cinacalcet hydrochloride, via (R)—N-(1-(naphthalen-1-yl)ethyl)-3-(3-(trifluoromethyl)phenyl) propanamide. U.S. Pat. No. 7,393,967 discloses a process for preparing Cinacalcet via coupling of 3-bromotrifluorotoluene with allylamine (R)—N-(1-(naphthalen-1-yl)ethyl)prop-2-en-1-amine in the presence of a catalyst and at least one base to obtain (R,E)-N-(1-(naphthalen-1-yl)ethyl)-3-(3-(trifluoromethyl)phenyl)prop-2-en-1-amine (CNC-ene) and reducing the unsaturated Cinacalcet to obtain Cinacalcet, as depicted in the following Scheme 6:

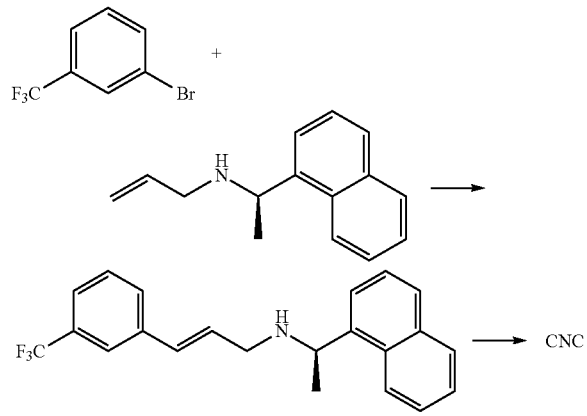

WO 2009/002427 discloses several methods for the preparation of Cinacalcet or salts thereof and polymorphs of Cinacalcet.

EP 2022777 describes a hydrogenation method for the preparation of Cinacalcet from the corresponding alkyne.

EP 1990333 discloses a multi step process, which comprises reacting an in-situ intermediate formed from 3-(trifluomethylphenyl)propionic acid and ethylchloroformate with a (R)-(+)-1-(1-naphthyl)ethylamine to give an amide intermediate which is then reduced to obtain Cinacalcet.

WO 2009/025792 provides crystalline forms of Cinacalcet fumarate and Cinacalcet succinate and processes for preparing said crystalline forms.

WO 2009/039241 provides a process for producing Cinacalcet hydrochloride, including: providing a Cinacalcet carboxylate salt, and converting said Cinacalcet carboxylate salt, more preferably Cinacalcet acetate, into Cinacalcet hydrochloride by means of an anion exchange reaction.

The present invention provides a novel and efficient process that leads to Cinacalcet, its pharmaceutically acceptable salts and intermediates thereof, which is convenient for the industrial scale and provides the desired product in good yields.

Accordingly, it is an object of the present invention to provide a method for preparing Cinacalcet hydrochloride and intermediates thereof, which can be used for mass production.

The present invention provides a process for the preparation of Cinacalcet hydrochloride and intermediates thereof, which proceeds essentially as depicted in the following Scheme 7:

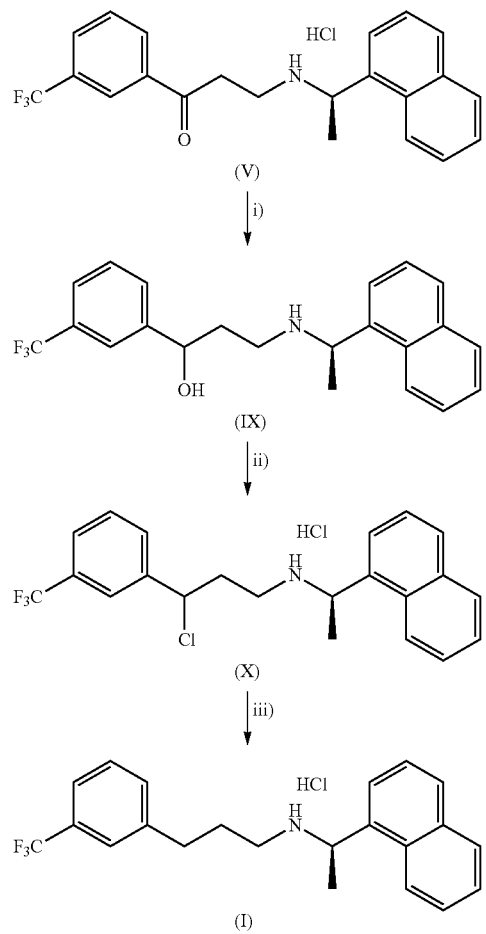

It is therefore an object of the present invention providing a process for preparing the Cinacalcet intermediate of formula (X)

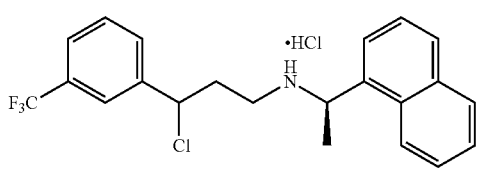

(X)

said process comprising:
i) reducing the compound of formula (V)

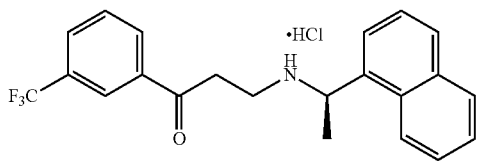

(V)

to give the compound of formula (IX)

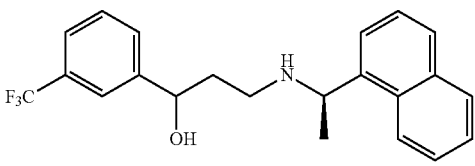

(IX)

and
ii) treating the compound of formula (IX) with a chlorinating agent.

In one aspect of the present invention, the compound of formula (IX) is not isolated from the reaction mixture.

In another aspect of the present invention, the compound of formula (IX) is isolated from the reaction mixture.

The compound of formula (IX) can exist as a free base or as a salt of an acid HZ, wherein Z is a pharmaceutically acceptable anionic counterion.

A "pharmaceutically acceptable anionic counterion" Z refers to a negatively charged molecule or atom that is balanced by the positively charged protonated Cinacalcet intermediate. A pharmaceutically acceptable anionic counterion may be organic or inorganic. For example, representative pharmaceutically acceptable anionic counterions include chloride, bromide, bisulfate (hydrogen sulfate), methanesulfonate, p-toluenesulfonate, phosphate, hydrogenphosphate, oxalate, formate, acetate, citrate, tartrate, succinate, maleate and malonate. Chloride, bisulfate, p-toluenesulfonate, tartrate and succinate are preferred; chloride is more preferred.

In a preferred aspect of the present invention, the compound of formula (IX) is isolated from the reaction mixture as a salt as disclosed here above.

As an example, the compound of formula (IX) wherein Z is chloride is the compound of formula (IXa)

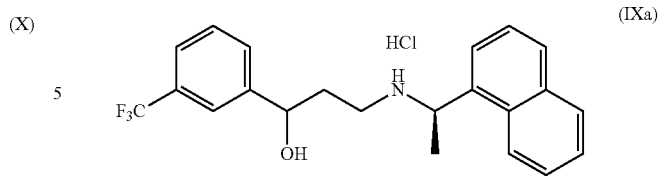

(IXa)

The reduction under step i) can be carried out in the presence of suitable reducing agents including sodium borohydride, lithium borohydride, diisobutyl aluminium hydride and 1,1,3,3-tetramethyldisiloxane in combination with a Lewis acid, for example $AlCl_3$, $TCl_4$, $FeCl_3$ or $ZnCl_2$. The reduction under step i) can be carried out with gaseous hydrogen in the presence of suitable reduction catalysts including Pd/C, $PtO_2$ (Adam's catalysts), Raney nickel and $PdCl_2$.

The reaction under step i) can be carried out in a solvent selected from, for example water, a linear or branched $C_1$-$C_5$ alcohol, such as, for example, methyl, ethyl, n-propyl, iso-propyl, n-butyl, sec-butyl or tert-butyl alcohol, a linear, branched or cyclic $C_4$-$C_8$ ether such as, for example, 1,2-dimethoxyetane, 2-methoxyethyl ether, diisopropyl ether, dibutyl ether, methyl tort-butyl ether, tetrahydrofuran (THF) or 1,4-dioxane, or a mixtures thereof; the suitable solvent being selected according to standard procedures well-known to a person skilled in the art, depending on the reducing agent. The reaction under step i) can be carried out at a temperature between −10° to 40° C., over a period of about 0.5 to 10 hours. When the catalyst Pd/C, $PtO_2$ or $PdCl_2$ is used, the $H_2$ pressure is typically 101.325 kPa. When Raney nickel is used, the $H_2$ pressure is moderately high (6,894.757 kPa). Typically, the hydrogenation is carried out over a period of about 5 to about 24 hours.

The reduction under step i) can be also carried out via catalytic transfer hydrogenation (CTH). When the reduction is carried out under CTH conditions, suitable hydrogen-bearing feed materials, such as, for example formic acid, ammonium formate or sodium formate, preferably ammonium formate or sodium formate are employed. In order to activate the hydrogen-bearing material as hydrogen donor, a catalyst as defined above is employed to promote the hydrogen transfer from hydrogen-bearing feed material to the substrate. CTH may be performed by any method known to a person skilled in the art. In particular, when CTH techniques are used in the reaction under step i), the compound of formula (V) is dissolved in a solvent selected from for example, toluene, acetic acid and a $C_1$-$C_5$ alcohol as defined above, preferably ethyl alcohol, in the presence of formic acid, ammonium formate or sodium formate, preferably ammonium formate or sodium formate, at refluxing temperature of the selected solvent, over a period of about 5 to 48 hours.

Preferably the reduction under step i) can be carried out by using sodium borohydride in methanol at a temperature ranging from −10° C. to 10° C.

The reaction under step ii) can be carried out with a suitable chlorinating agent selected from the group comprising thionyl chloride ($SOCl_2$), phosphorous pentachloride ($PCl_5$), phosphorous oxychloride ($POCl_3$), oxalyl chloride (($ClCO)_2$), gaseous hydrochloric acid, phosgene ($Cl_2CO$), and non-gaseous oligomeric equivalents of phosgene such as trichloromethyl chloroformate (diphosgene, liquid) and bis (trichloromethyl)carbonate (triphosgene, BTC, solid) which act as phosgene source in situ. The solvents that can be employed under step ii) can be selected from the group comprising $C_3$-$C_7$ linear, branched and cyclic aliphatic hydrocarbon solvents including hexane, heptane, cyclopentane, cyclohexane, cycloheptane, and mixtures thereof; aromatic hydrocarbons including benzene, toluene, xylenes, preferred being toluene and xylenes, most preferred being toluene; linear, branched and cyclic ethers including methyl tert-butyl, diisopropyl, di-n-butyl ether, THF and methyl-THF; aprotic solvents including hexamethylphosphoramide (HMPA) and 1,3-dimethyl-3,4,5,6-tetrahydro-2(1H)-pyrimidinone (DMPU).

The reaction under step ii) may be carried out at a temperature that ranges from about 0° C. to the boiling point of the solvent, over a period of about 1 hour to 24 hours. Preferably, the reaction under step ii) is carried out by using thionyl chloride or phosphorous oxychloride ($POCl_3$) as the chlorinating agent, in toluene, at a temperature ranging from 10° to 50° C., for a time ranging from 1 hour to 12 hours. In a most preferred embodiment, the reaction under step ii) is carried out using thionyl chloride in toluene, operating at 30° C. for 3 hours.

When the compound of formula (IX) is isolated from the reaction mixture, preferably in the form of a salt of an acid HZ as defined above, the reaction under step ii) can be preferably carried out with a solvent selected from, for example, cyclohexane, toluene, xylene, dichloromethane, THF, or hexamethylphosphoramide (HMPA), at a temperature between 10° C. to the boiling point of the selected solvent, over a period of about 1 hour to 24 hours. Preferably, the salt of the compound of formula (IX) is the hydrochloride salt.

When the compound of formula (IX) is not isolated from the reaction mixture, the reaction under step ii) can be preferably carried out with a solvent selected from, for example, cyclohexane, toluene, xylene, dichloromethane, 1,2-dichloroethane, methyl tert-butyl, diisopropyl, di-n-butyl ether, THF, methyl-THF or hexamethylphosphoramide (HMPA), at a temperature between 0° and 70° C., over a period of about 1 hour to 24 hours.

In one embodiment, the reaction under step ii) produces the intermediate of formula (X) while generating a certain amount of the compound of formula (XI)

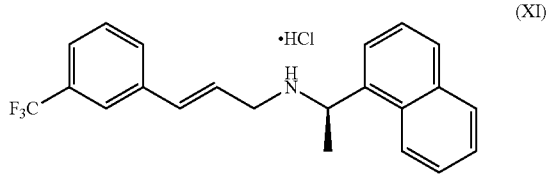
(XI)

The compound of formula (X) or a mixture of compounds of formulae (X) and (XI) can then be used for preparing Cinacalcet hydrochloride of formula (I).

Furthermore, the present invention encompasses a process for preparing Cinacalcet hydrochloride, by preparing the Cinacalcet intermediate of formula (X) or a mixture of compounds of formulae (X) and (XI) as described above, and converting it to Cinacalcet hydrochloride of formula (I).

It is therefore a further object of the present invention a process for preparing Cinacalcet hydrochloride of formula (I)

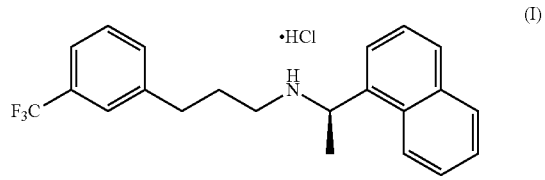 [SMILES: C[C@@H](NCCCc1cccc(C(F)(F)F)c1)c1cccc2ccccc12 ; Cl]
(I)

which comprises the steps of
i) reducing the compound of formula (V)

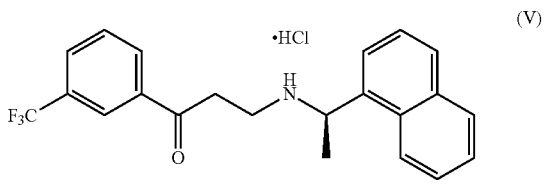 [SMILES: C[C@@H](NCCC(=O)c1cccc(C(F)(F)F)c1)c1cccc2ccccc12 ; Cl]
(V)

to give the compound of formula (IX)

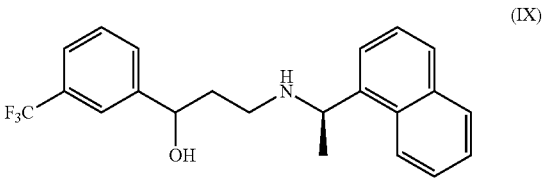 [SMILES: C[C@@H](NCCC(O)c1cccc(C(F)(F)F)c1)c1cccc2ccccc12]
(IX)

ii) treating the compound of formula (IX) with a chlorinating agent to give the compound of formula (X), which can be in admixture with the compound of formula (XI); and

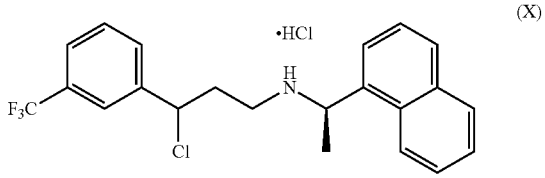
(X)

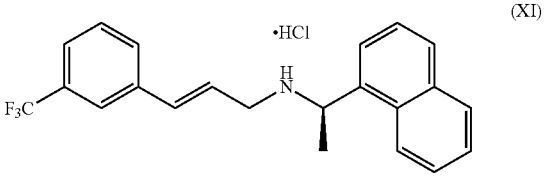 [SMILES: C[C@@H](NC/C=C/c1cccc(C(F)(F)F)c1)c1cccc2ccccc12 ; Cl]
(XI)

iii) converting the compound of formula (X) or, if the case, the compound of formula (X) mixed with the compound of formula (XI) into Cinacalcet hydrochloride of formula (I).

The conversion under step iii) of the compound of formula (X) or, if the case, the compound of formula (X) mixed with the compound of formula (XI), can be carried out with an acidic proton source selected from aqueous hydrochloric acid or glacial acetic acid, preferably 30% hydrochloric acid, and elemental Zn. The solvents that can be employed under step iii) are selected from the group comprising water; linear and branched $C_1$-$C_4$ alcohols selected from the group comprising methyl, ethyl, n-propyl, iso-propyl, n-butyl, sec-butyl and tert-butyl alcohol; linear, branched and cyclic ethers selected from the group comprising methyl tert-butyl, diisobutyl, di-n- butyl ether, THF, methyl-THF and mixtures thereof; at a temperature ranging from 0° to 60° C. Preferably, the reaction under step iii) can be carried out in ethanol or THF/water mixtures at a temperature of about 25° C.

Alternatively, the conversion under step iii) can be carried out by catalytic hydrogenation, i.e. with molecular hydrogen in the presence of a catalyst selected from Pd/C, PtO$_2$, Raney nickel and PdCl$_2$, preferably Pd/C. The catalytic hydrogenation may be performed by any method known to a person skilled in the art. For example, the compound of formula (X) or, if the case, the compound of formula (X) mixed with the compound of formula (XI), may be dissolved in a suitable solvent and exposed to H$_2$ pressure, in the presence of a catalyst such as, for example, Pd/C, PtO$_2$ (Adam's catalysts), Raney nickel or PdCl$_2$. When the catalyst is selected from Pd/C, PtO$_2$ or PdCl$_2$, the H$_2$ pressure is chosen in the range of from 50.66 to 506.62 kPa, while when the catalyst is Raney nickel, the H$_2$ pressure is chosen in a higher range from 405.3 to 7092.75 kPa. The suitable solvent can be selected from the group comprising a C$_2$-C$_5$ nitrile such as, for example, acetonitrile; a linear or branched C$_1$-C$_4$ alcohol such as, for example, methyl, ethyl, n-propyl, iso-propyl, n-butyl, sec-butyl or tert-butyl alcohol; a linear or branched C$_3$-C$_9$ ketone such as, for example, methylethyl or methylisobutyl ketone; a linear or branched C$_3$-C$_7$ ester such as, for example, ethyl, iso-propyl or n-butyl acetate; toluene and mixtures thereof. Preferably, the solvent can be selected from the group consisting of methanol, ethanol, isopropanol, ethyl acetate and mixtures thereof; more preferably the solvent is methanol. Typically, the hydrogenation is carried out over a period of about 1 hour to 96 hours. Reaction temperature may range from 0° to 50° C., preferably from 10° to 30° C., most preferably the hydrogenation is carried out at 20° C.

In a preferred aspect, the conversion under step iii) is carried out by dissolving compound (X) or, if the case, the compound of formula (X) mixed with the compound of formula (XI), in methanol and exposing the mixture to 100 kPa hydrogen gas, at 20° C. in the presence of 0.5%-1% mol/mol Pd/C.

The conversion under step iii) can also occur in an efficient way when the compound of formula (X) is present as free base.

In a particular aspect, the present invention provides free-basing the compound of formula (X), before converting it into Cinacalcet hydrochloride. The compound of formula (X) as a free base is preferably not isolated from the reaction mixture before its conversion into Cinacalcet hydrochloride.

The compound of formula (X) is therefore converted into the corresponding free-base by reaction with an aqueous base selected from the group comprising sodium hydroxide, potassium hydroxide, sodium carbonate, potassium carbonate, sodium hydrogencarbonate and potassium hydrogencarbonate, and extracted in an organic solvent, such as for example, toluene, ethyl acetate, isopropyl acetate or MTBE, before being converted into Cinacalcet hydrochloride. Alternatively, the compound of formula (X) is dissolved in methanol in the presence of an inorganic base, such as, for example, sodium carbonate, potassium carbonate, sodium hydrogencarbonate or potassium hydrogencarbonate.

In a preferred embodiment, the compound of formula (X) is free-based with aqueous sodium hydrogencarbonate, extracted in toluene and then exposed to 100 kPa hydrogen in a toluene/methanol or toluene/acetone mixture, at a temperature of 20° C., in the presence of Pd/C. In another preferred embodiment, the compound of formula (X) is dissolved in methanol and the reaction is carried out by pressurizing to 100 kPa with hydrogen in the presence of Pd/C and a stoichiometric amount of sodium hydrogencarbonate, at a temperature of 20° C.

The present invention also includes a one-pot process for the preparation of Cinacalcet hydrochloride without isolation of intermediates; in particular, the intermediate of formula (IX) is prepared and used in situ without isolation.

The compound of formula (V) as defined above can be prepared according to the methods described in ZaCh System's co-pending International patent application No. WO 2010/049293, for example, as reported in the following Reference Example 1. The present invention is exemplified by the following examples, which are provided for illustration only and should not be construed to limit the scope of the invention.

REFERENCE EXAMPLE 1

Synthesis of (R)-3-(1-(naphthalen-1-yl)ethylamino)-1-(3-(trifluoromethyl)phenyl)propan-1-one hydrochloride salt (V)

Method A

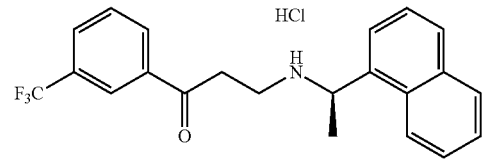 [SMILES: C[C@@H](NCCC(=O)c1cccc(C(F)(F)F)c1)c1cccc2ccccc12 ; Cl]

(R)-(1-naphthyl)ethylamine hydrochloride (100.0 g), paraformaldehyde (15.9 g), 3-(trifluoromethyl)acetophenone (135.7 g), 30% w/w aqueous hydrochloric acid (5.6 g), ethanol (150.0 g) and water (10.0 g) were charged into the reactor and stirred at reflux for 14 hrs, until satisfactory conversion was observed via HPLC. Then water (300.0 g) and toluene (305.0 g) were added and the mixture was stirred at 25° C. The organic and aqueous layers were separated and additional water (200.0 g) was charged over the organic phase in order to favour the precipitation. The title compound (95.6 g) was isolated upon filtration at room temperature, washing with water and methyl tert-butyl ether and exsiccation at 50° C.

NMR of R)-3-(1-(naphthalen-1-yl)ethylamino)-1-(3-(trifluoromethyl)-phenyl)-propan-1-one hydrochloride salt (V)

$^1$H NMR (400 MHz, DMSO-d$_6$), δ (ppm, TMS): 10.00 (1H, br s; —NH$_2^+$—), 9.24 (1H, br s; —NH$_2^+$—), 8.31 (1H, d, J=8.4; ArH), 8.23 (1H, d, J=8.0 Hz; ArH), 8.16 (1H, br s; ArH), 8.08-7.96 (4H, m; ArH), 7.82 (1H, t, J=8.0 Hz; ArH), 7.69-7.58 (3H, m; ArH), 5.47-5.36 (1H, m; —CH(CH$_3$)—), 3.70-3.54 (2H, m; —CH$_2$—), 3.41-3.26 (2H, m; —CH$_2$—), 1.72 (3H, m, J=6.4 Hz; —CH(CH$_3$)—).

Method B (R)-(1-naphthyl)ethylamine hydrochloride (1.5 g), paraformaldehyde (0.3 g), 3-(trifluoromethyl)acetophenone (1.8 g), 30% w/w aqueous hydrochloric acid (0.1 g), ethanol (4.5 g) and water (1.5 g) were charged into the reactor under stirring and reacted for 5 minutes under microwave irradiation (max 250 W), until satisfactory conversion was observed via HPLC. Then water (10.0 g) and toluene (3.0 g) were added and the resulting suspension was stirred at 25° C. The title compound (1.6 g) was isolated upon filtration at room temperature, washing with water and methyl 2-propanol and exsiccation at 50° C.

EXAMPLE 1

Synthesis of (R)-3-(1-(naphthalen-1-yl)ethylamino)-1-(3-(trifluoromethyl)phenyl)propan-1-ol hydrochloride (IXa)

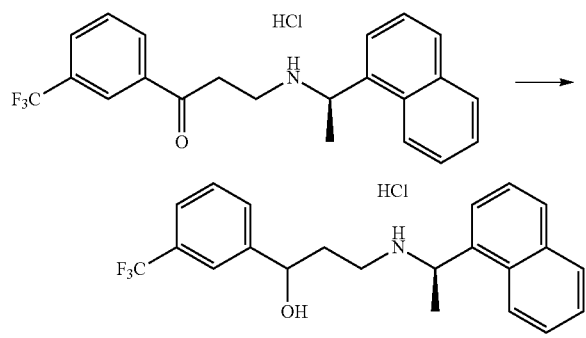

(R)-3-(1-(naphthalen-1-yl)ethylamino)-1-(3-(trifluoromethyl)phenyl)propan-1-one hydrochloride (V) (15.95 g, 39.104 mmol) is suspended in cold methanol (50 ml) at −10° C. and, subsequently, a solution of sodium borohydride (0.75 g, 19.610 mmol), 30% w/w aqueous sodium hydroxide (5.74 g, 43.014 mmol) and water (5 ml) is added slowly in order to keep the internal temperature below 0° C. The reaction mixture is stirred at 0° C. for 0.5 hrs and then quenched by addition of 30% w/w aqueous hydrochloric acid up to pH=1, followed by water (40 ml), and allowed to reach room temperature. The so-formed thick suspension is heated up to 50° C., stirred for 20 minutes and then cooled down to 5° C. The precipitate is filtered, washed with a 9:1 vol/vol water/methanol mixture (10 ml) and dried at 50° C. under vacuum. 14.69 g (35.841 mmol) of high quality (R)-3-(1-(naphthalen-1-yl)ethylamino)-1-(3-(trifluoromethyl)phenyl)propan-1-ol hydrochloride (IXa) are obtained (yield: 91.7%; white powder).

EXAMPLE 2

Synthesis of (R)-3-chloro-N-(1-(naphthalen-1-yl)ethyl)-3-(3-(trifluoromethyl)phenyl)propan-1-amine hydrochloride (X)

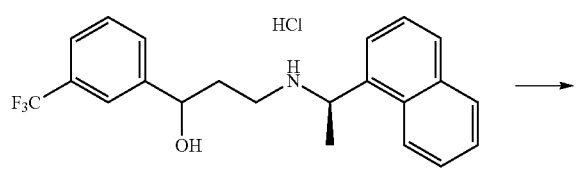

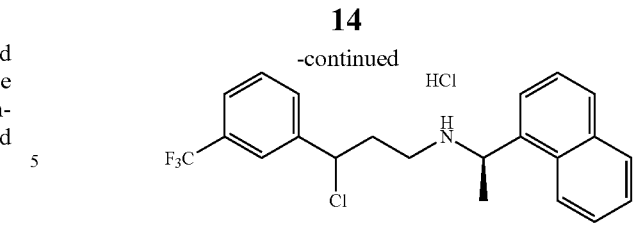

(R)-3-(1-(naphthalen-1-yl)ethylamino)-1-(3-(trifluoromethyl)phenyl)propan-1-ol hydrochloride (IXa) (20.0 g, 48.796 mmol) is suspended in toluene (140 ml) at 40° C. and phosphoryl chloride (4.3 g, 28.044 mmol) is added drop-wise over 10 minutes. The reaction mixture is stirred two hours at 60° C., then DMF (1.0 g) is added at 40° C., followed by additional phosphoryl chloride (3.2 g, 20.870 mmol). The mixture is stirred at 40° C. overnight and then MTBE (40 ml) is added. Volatiles are removed by repeatedly distilling off under vacuum and restoring MTBE. After that a 1:1 vol/vol toluene/MTBE solution is received, which is heated up to 70° C. and allowed to cool down slowly to 15°-20° C. the so-obtained precipitate is aged at room temperature overnight, then filtered and washed with a 1:1 vol/vol toluene/MTBE mixture (3×12 ml). (R)-3-chloro-N-(1-(naphthalen-1-yl)ethyl)-3-(3-(trifluoromethyl)phenyl)propan-1-amine hydrochloride (X) is obtained as a white powder after exsiccation at 55° C. under vacuum (6.0 g, 14.008 mmol, yield: 28.7%).

EXAMPLE 3

Synthesis of (R)-3-chloro-N-(1-(naphthalen-1-yl)ethyl)-3-(3-(trifluoromethyl)phenyl)propan-1-amine hydrochloride (X) and (R,E)-N-(1-(naphthalen-1-yl)ethyl)-3-(3-(trifluoromethyl)phenyl)prop-2-en-1-amine hydrochloride (XI)

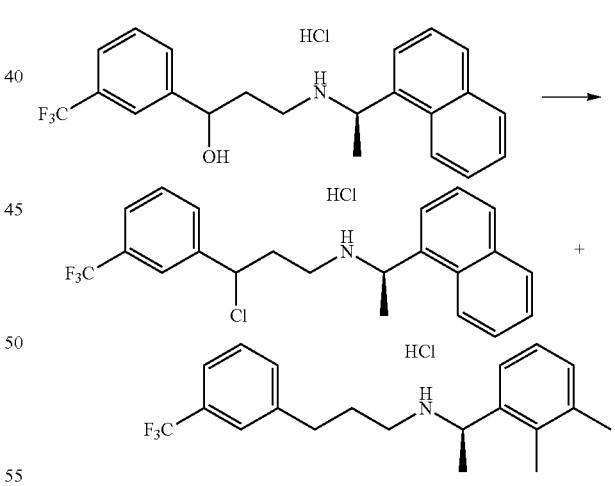

Method A (R)-3-(1-(naphthalen-1-yl)ethylamino)-1-(3-(trifluoromethyl)phenyl)propan-1-ol hydrochloride (IX) (35.0 g, 85.393 mmol) is suspended in toluene (150 ml) at 20° C. and thionyl chloride (11.2 g, 94.141 mmol) is added slowly. The reaction mixture is stirred at 30°-40° C. for 4-5 hrs and then the solvent is distilled off under vacuum. The residual toluenic slurry is flushed with isopropanol, upon several distillation/refill cycles. The resulting isopropanol solution is refluxed for 1 hr, then cooled down to 45° C. and added with methyl tert-butyl ether (MTBE) (70 ml). The so-obtained suspension is stirred at 45° C. for 1 hr, then cooled down to 0° C. and aged 1 hr. 29.6 g of a 95.8:4.2 (HPLC % area) mixture of (R)-3-chloro-N-(1-(naphthalen-1-yl)ethyl)-3-(3-(trifluoromethyl)phenyl)propan-1-amine hydrochloride (X) and (R,E)-N-(1-(naphthalen-1-yl)ethyl)-3-(3-(trifluoromethyl)phenyl)prop-2-en-1-amine hydro-chloride (XI) is obtained as a white powder after filtration, washing with a 3:1 vol/vol isopropanol/MTBE mixture (2×20 ml) end exsiccation at 55° C. under vacuum.

Method B (R)-3-(1-(naphthalen-1-yl)ethylamino)-1-(3-(trifluoromethyl)phenyl)propan-1-ol hydrochloride (IX) (50.0 g, 121.990 mmol) is suspended in MTBE (200 ml) and water (80 ml) at room temperature. Sodium hydroxide (30% w/w aqueous solution) is added drop-wise (17.1 g, 128.250 mmol) in order to control the exothermic reaction and the mixture is stirred until the starting solid dissolves completely. The organic layer is then separated and washed repeatedly with water up to neutral pH. Thus MTBE is flushed with toluene and thionyl chloride (16.7 g, 140.372 mmol) is added slowly to the resulting toluenic solution, while maintaining 10°-20° C. The reaction mixture is heated up to 60° C. and maintained for 4 hrs, or until positive IPC (via HPLC). At reaction completion MTBE is charged (170 ml) and the mixture is heated up to 80°-85° C. and trace water is removed azeotropically. The mixture is cooled down to 60° C., MTBE is restored, then cooled down to 10° C. and aged two hours. 46.1 g of a 96.2:3.8 (HPLC % area) mixture of (R)-3-chloro-N-(1-(naphthalen-1-yl)ethyl)-3-(3-(trifluoromethyl)phenyl)propan-1-amine hydrochloride (X) and (R,E)-N-(1-(naphthalen-1-yl)ethyl)-3-(3-(trifluoromethyl)phenyl)prop-2-en-1-amine hydrochloride (XI) is obtained as a white powder after filtration, washing with a 1:1 vol/vol toluene/MTBE mixture (3×40 ml) end exsiccation at 55° C. under vacuum.

EXAMPLE 4

One-pot synthesis of (R)-3-chloro-N-(1-(naphthalen-1-yl)ethyl)-3-(3-(trifluoromethyl)phenyl)propan-1-amine hydrochloride (X) and (R,E)-N-(1-(naphthalen-1-yl)ethyl)-3-(3-(trifluoromethyl)phenyl)prop-2-en-1-amine hydrochloride (XI)

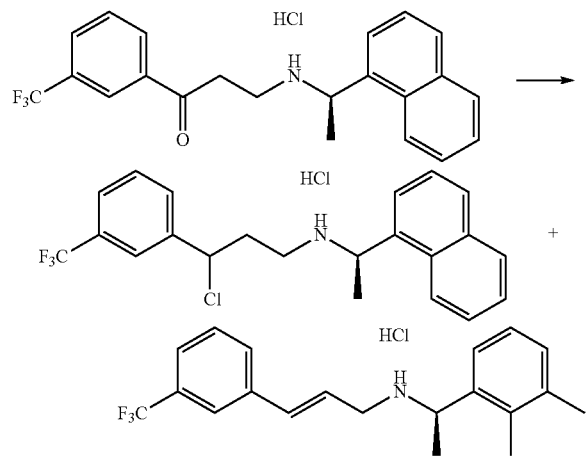

(R)-3-(1-(naphthalen-1-yl)ethylamino)-1-(3-(trifluoromethyl)phenyl)propan-1-one hydrochloride (V) (100.0 g, 245.182 mmol) is suspended in cold methanol (50 ml) at −10° C. and, subsequently, a solution of sodium borohydride (4.6 g, 121.597 mmol), 30% w/w aqueous sodium hydroxide (35.5 g, 266.250 mmol) and water (30 ml) is added slowly in order to keep the internal temperature below 0° C. The reaction mixture is stirred at 0° C. for 0.5 hrs, then quenched by addition of acetic acid (36.7 g, 611.157 mmol), allowed to reach room temperature and added with water (280 ml). The volatile solvent is distilled off under vacuum at 40° C., then MTBE is charged (400 ml). The organic layer is separated and washed with water (3×50 ml). Then the free base is liberated by addition of sodium hydroxide (aq. 30% w/w; 48.8 g, 366.0 mmol) up to pH=12-13, and the organic layer is washed with water (3×50 ml). MTBE is distilled off under vacuum and flushed with toluene. The reaction mixture is then cooled down to 20° C. and a solution of thionyl chloride (30.5 g, 256.367 mmol) in toluene (60 ml) is charged drop-wise over two hours. The mixture is then stirred at 30° C. for 3 hours and once reaction goes to completion the volatiles are removed under vacuum at 60° C. Then toluene is restored and the reaction mixture is cooled to 20° C. Diisopropyl ether (200 ml) is added and the reaction mixture is refluxed at 80° C. for 1 hour, then cooled down to 20° C. The resulting thick suspension is filtered, the solid is washed with a 2:1 vol/vol toluene/diisopropyl ether (60 ml), followed by MTBE (3×60 ml). The so-formed thick suspension is heated up to 50° C., stirred for 20 minutes and then cooled down to 5° C. 65.0 g of a 98.4:1.6 (HPLC % area) mixture of (R)-3-chloro-N-(1-(naphthalen-1-yl)ethyl)-3-(3-(trifluoromethyl)phenyl)propan-1-amine hydro-chloride (X) and (R,E)-N-(1-(naphthalen-1-yl)ethyl)-3-(3-(trifluoromethyl)phenyl)-prop-2-en-1-amine hydrochloride (XI) is obtained as a white powder after exsiccation at 55° C. under vacuum.

EXAMPLE 5

Synthesis of (R)—N-(1-(naphthalen-1-yl)ethyl)-3-(3-(trifluoromethyl)phenyl)propan-1-amine hydrochloride (I) (Cinacalcet hydrochloride)

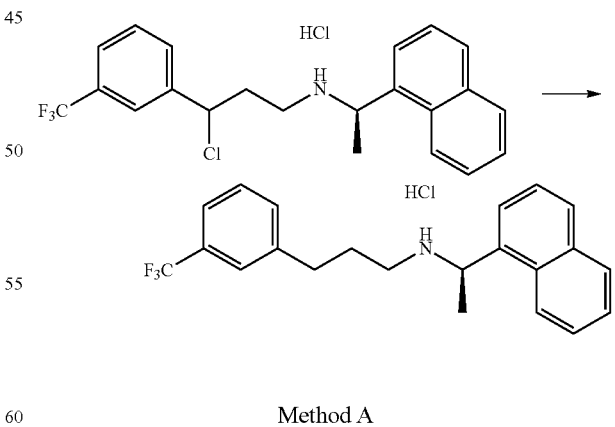

Method A (R)-3-chloro-N-(1-(naphthalen-1-yl)ethyl)-3-(3-(trifluoromethyl)phenyl)propan-1-amine hydrochloride (X) (15.0 g, 35.021 mmol), methanol (150 ml), heterogeneous catalyst and eventually an additive are charged into an autoclave, exposed to an inert atmosphere and then pressurized with 100 kPa hydrogen gas, under stirring at 20° C. Once the reaction is complete (IPC via HPLC), the final product (Cinacalcet hydrochloride) is isolated after filtration through a Celite® pad, solvent removal and, eventually, recrystallization according to the teachings of Example 13 of the International patent application No. WO 2010/094674 in the cases where no additive is employed. In the case sodium bicarbonate is used in the reaction mixture as a hydrogen chloride quencher, water is added and then the reaction mixture is filtered through a Celite® pad. After that methanol is removed under vacuum, isopropyl acetate (150 ml) is added and 30% w/w sodium hydroxide is charged until the starting suspension dissolves completely. The organic layer is then separated, washed with water up to neutral pH, treated with 30% w/w aqueous hydrochloric acid up to pH 2-3 and concentrated in order to give Cinacalcet hydrochloride, which is optionally recrystallized from ether or ester solvents or mixtures thereof with small amounts of alcoholic solvent (see the following table for detailed results).

| Catalyst | Cat., % | Additive/equiv. | Time, hrs | Conv., % |
|---|---|---|---|---|
| 5% Pd/C[(1)] | 0.5 | — | 96 | 99.5 |
| 5% Pd/C[(1)] | 0.9 | — | 43 | 98.6 |
| 5% Pd/C[(1)] | 0.5 | $NaHCO_3$/0.95 | 9 | 99.7 |
| Pd(Pb)/CaCO$_3$ | 5.0 | $NaHCO_3$/0.95 | 5 | 32.5 |
| PdCl$_2$ | 5.0 | $NaHCO_3$/0.95 | 9 | 97.9 |
| Raney Ni | 5.0 | — | 7 | 13.6 |
| PdCl$_2$ | 5.0 | — | 8 | 89.0 |

[(1)] 5% Pd/C Engelhard 5398: catalyst specifically optimized for N,O-debenzylation reactions
[(2)] 5% Pd/C Engelhard 5016

Method B (R)-3-chloro-N-(1-(naphthalen-1-yl)ethyl)-3-(3-(trifluoromethyl)phenyl)propan-1-amine hydro-chloride (X) (5.0 g, 11.674 mmol), is suspended in alcoholic solvent or water/THF mixtures (40 ml) at 25° C. Proton-source acidic additive (7-8 equiv.) is charged followed by zinc powder (2.5-3.5 equiv.), added portion-wise. Gas evolution, exothermic reaction and dissolution of the starting material are observed and the reaction mixture is stirred at 25° C. until complete consumption of zinc is achieved. The reaction course is monitored via HPLC (see the following table for detailed results).

| Proton Source | Solvent | Time, hrs | Conv., % |
|---|---|---|---|
| 3.0 aq. HCl | MeOH | 22 | 99.7 |
| 3.0 aq. HCl | EtOH | 22 | 97.9 |
| 3.0 aq. HCl | THF/H$_2$O | 22 | 90.9 |
| 3.0 HOAc | THF/H$_2$O | 22 | 99.8 |

Method C (R)-3-chloro-N-(1-(naphthalen-1-yl)ethyl)-3-(3-(trifluoromethyl)phenyl)propan-1-amine hydro-chloride (X) (10.0 g, 23.347 mmol) is dissolved in methanol (100 ml) and palladium chloride (0.124 g, 0.699 mmol) is added at 20° C. Triethylsilane (7.4 g, 63.639 mmol) is charged slowly over 20 minutes, in order to control the exothermic reaction and then the reaction mixture is stirred at 20° C. After 18 hours a 94% conversion is observed via HPLC.

Method D (R)-3-chloro-N-(1-(naphthalen-1-yl)ethyl)-3-(3-(trifluoromethyl)phenyl)propan-1-amine hydro-chloride (X) (15.0 g, 35.021 mmol) is suspended in toluene (90 ml) at 15°-20° C. and sat. aq. sodium bicarbonate (75.6 g, X72 mmol) is charged drop-wise, under vigorous stirring, until pH=8-9 of the aqueous layer. The mixture is layered upon standing few minutes and then the organic phase is separated, washed with water (2×75 ml) and transferred into an autoclave. 5% Palladium on carbon (50% moisture content) is added (0.373 g, 0.088 mmol), followed by methanol (15 ml), the mixture is exposed to inert atmosphere, then pressurized with 100 kPa hydrogen gas, upon stirring at 20° C. Hydrogen pressure is maintained until positive IPC (via HPC, about 4-5 hrs), then the reaction mixture is filtered through a Celite® pad. Methanol is distilled off the filtered solution and isopropyl acetate (IPAC) (90 ml) is added. The resulting suspension is heated up to 70° C. and stirred for 30 minutes, then cooled down slowly to 0° C. Cinacalcet hydrochloride is isolated as a white powder upon filtration, washing with IPAC (2×15 ml) and exsiccation at 60*-65° C. under vacuum (11.4 g, 28.944 mmol; yield: 82.6%).

The invention claimed is:
1. Cinacalcet intermediate having the following formula (X)

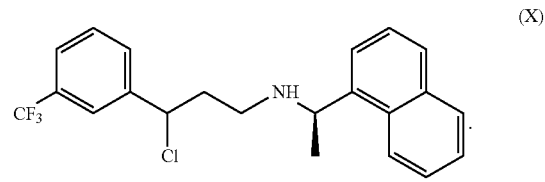 [SMILES: C[C@@H](NCCC(Cl)c1cccc(C(F)(F)F)c1)c1cccc2ccccc12]

2. A process for the preparation of Cinacalcet intermediate of formula (X) as defined in claim 1, which comprises the steps of:
   i) reducing the compound of formula (V)

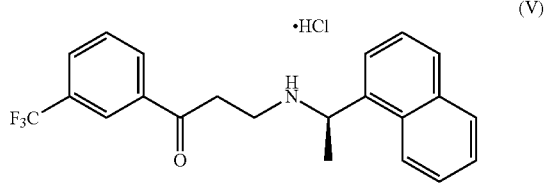 [SMILES: Cl ; C[C@@H](NCCC(=O)c1cccc(C(F)(F)F)c1)c1cccc2ccccc12]

to give the compound of formula (IX)

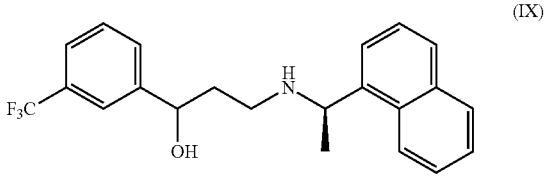 [SMILES: C[C@@H](NCCC(O)c1cccc(C(F)(F)F)c1)c1cccc2ccccc12]

and
   ii) treating the compound of formula (IX) with a chlorinating agent selected from the group comprising thionyl chloride (SOCl$_2$), phosphorous pentachloride (PCl$_5$), phosphorous oxychloride (POCl$_3$), oxalyl chloride ((ClCO)$_2$), gaseous hydrochloric acid, phosgene (Cl$_2$CO), and non-gaseous oligomeric equivalents of phosgene such as trichloromethyl chloroformate (diphosgene, liquid) and bis(trichloromethyl)carbonate (triphosgene, BTC, solid), which act as phosgene source in situ.

3. A process according o claim 2, wherein the chlorinating agent is thionyl chloride (SOCl$_2$) or phosphorous oxychloride (POCl$_3$).

4. A process according to claim 2, wherein the compound of formula (IX) is not isolated from the reaction mixture.

5. A process according to claim 2, wherein the compound of formula (IX) is isolated from the reaction mixture in the form of a salt with an acid HZ, wherein Z is a pharmaceutically acceptable anionic counterion selected from the group comprising: chloride, bromide, bisulfate (hydrogen sulfate), methanesulfonate, p-toluenesulfonate, phosphate, hydrogenphosphate, oxalate, formate, acetate, citrate, tartrate, succinate, maleate and malonate.

6. A process according to claim 5, wherein Z is chloride.

7. A process for the preparation of Cinacalcet hydrochloride of formula (I), which comprises the steps of preparing the compound of formula (X) according to claim 2 and converting it to Cinacalcet hydrochloride.

8. A process for preparing Cinacalcet hydrochloride of formula (I)

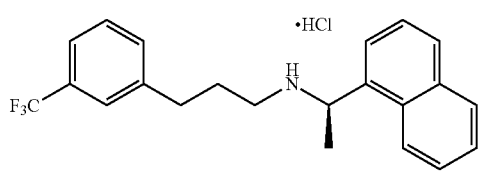

(I)

which comprises the steps of:
i) reducing the compound of formula (V)

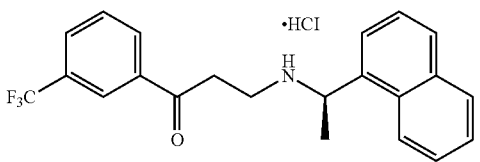

(V)

to give the compound of formula (IX)

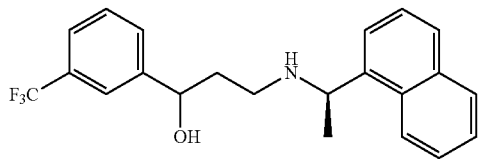

(IX)

ii) treating the compound of formula (IX) with a chlorinating agent selected from the group comprising thionyl chloride (SOCl$_2$), phosphorous pentachloride (PCl$_5$), phosphorous oxychloride (POCl$_3$), oxalyl chloride ((ClCO)$_2$), gaseous hydrochloric acid, phosgene (Cl$_2$CO), and non-gaseous oligomeric equivalents of phosgene such as trichloromethyl chloroformate (diphosgene, liquid) and bis(trichloromethyl)carbonate (triphosgene, BTC, solid), which act as phosgene source in situ., to give the compound of formula (X), which can be in admixture with the compound of formula (XI), and

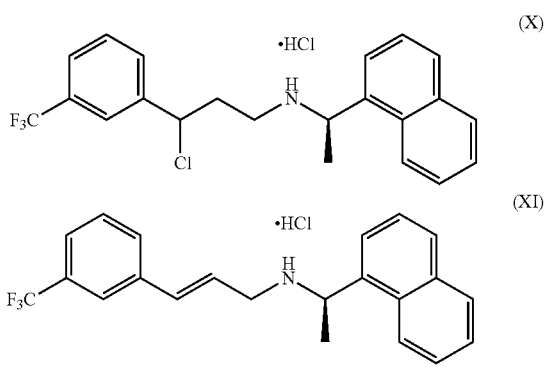

iii) converting the compound of formula (X) or, if the case, the compound of formula (X) mixed with the compound of formula (XI) into Cinacalcet hydrochloride of formula (I).

9. A process according to claim 8, wherein the conversion under step iii) is carried out with an acidic proton source selected from aqueous hydrochloric acid and glacial acetic acid, and Zn.

10. A process according to claim 9, wherein the acidic proton source is hydrochloric acid.

11. A process according to claim 8, wherein the conversion under step iii) is carried out with molecular hydrogen in the presence of a catalyst.

12. A process according to claim 11, wherein the catalyst is selected from the group comprising Pd/C, PtO$_2$, Raney nickel and PdCl$_2$.

13. A process according to claim 12, wherein the catalyst is Pd/C.

14. A process according to claim 11, wherein the conversion is carried out in the presence of an additive.

15. A process according to claim 14, wherein the additive is NaHCO$_3$.

16. A process according to claim 8, wherein the compound of formula (X) is free-based, before converting it to Cinacalcet hydrochloride under step iii).

17. A process according to claim 16, wherein the compound of formula (X) as a free base is not isolated from the reaction mixture.

18. A process according to claim 8, wherein the intermediate of formula (IX) is prepared and used in situ without isolation.

* * * * *